(12) United States Patent
Oliver et al.

(10) Patent No.: US 7,021,854 B2
(45) Date of Patent: Apr. 4, 2006

(54) SURGICAL ARM ASSEMBLY INCLUDING QUICK CONNECT MECHANISM

(75) Inventors: Dana Andrew Oliver, Plymouth, MA (US); Brian Keith Wells, Marietta, GA (US)

(73) Assignee: Teleflex-CT Devices Incorporated, Mansfield, MA (US)

( * ) Notice: Subject to any disclaimer, the term of this patent is extended or adjusted under 35 U.S.C. 154(b) by 0 days.

(21) Appl. No.: 10/720,143

(22) Filed: Nov. 25, 2003

(65) Prior Publication Data

US 2004/0165937 A1    Aug. 26, 2004

Related U.S. Application Data

(63) Continuation of application No. 10/040,679, filed on Nov. 8, 2001, now abandoned.

(51) Int. Cl.
*F16D 3/80* (2006.01)

(52) U.S. Cl. .................. 403/31; 403/321; 403/322.1; 403/DIG. 4; 600/227; 600/228; 600/229

(58) Field of Classification Search .............. 600/1, 600/102, 130, 200, 227–230; 403/321, 322.1, 403/322.2, 325, DIG. 4, 327, 31; 285/308, 285/314, 316
See application file for complete search history.

(56) References Cited

U.S. PATENT DOCUMENTS

| 2,608,192 | A | * | 8/1952 | Heitmeyer et al. | |
| 3,499,223 | A | * | 3/1970 | Lieb et al. | 433/129 |
| 3,624,905 | A | * | 12/1971 | Barsby | 433/82 |
| 3,638,973 | A | * | 2/1972 | Poletti | |
| 3,986,692 | A | * | 10/1976 | Kinoshita | |
| 4,318,695 | A | * | 3/1982 | Lieb et al. | 433/132 |
| 4,403,959 | A | * | 9/1983 | Hatakeyama | 433/126 |
| 4,863,133 | A | * | 9/1989 | Bonnell | |
| 5,336,089 | A | * | 8/1994 | Sakurai | 433/126 |
| 5,609,565 | A | * | 3/1997 | Nakamura | 600/229 |
| 5,918,844 | A | * | 7/1999 | Ognier | |
| 6,491,273 | B1 | * | 12/2002 | King et al. | 248/276.1 |
| 6,632,170 | B1 | * | 10/2003 | Bohanan et al. | |

FOREIGN PATENT DOCUMENTS

EP           415417 A2  *  3/1991

* cited by examiner

*Primary Examiner*—Daniel P. Stodola
*Assistant Examiner*—Michael P. Ferguson
(74) *Attorney, Agent, or Firm*—Baker Hostetler LLP

(57) ABSTRACT

A surgical arm system for holding and positioning one or more instruments during a surgical procedure includes at least one quick connect mechanism that beneficially allows for simple and expeditious, yet reliable disassembly and reassembly of the arm by any member of a surgical team without difficulty and without requiring additional tools, but while still ensuring that, following reassembly, the arm is structurally sound, properly dimensioned, and capable of functioning in a highly reliable manner.

23 Claims, 11 Drawing Sheets

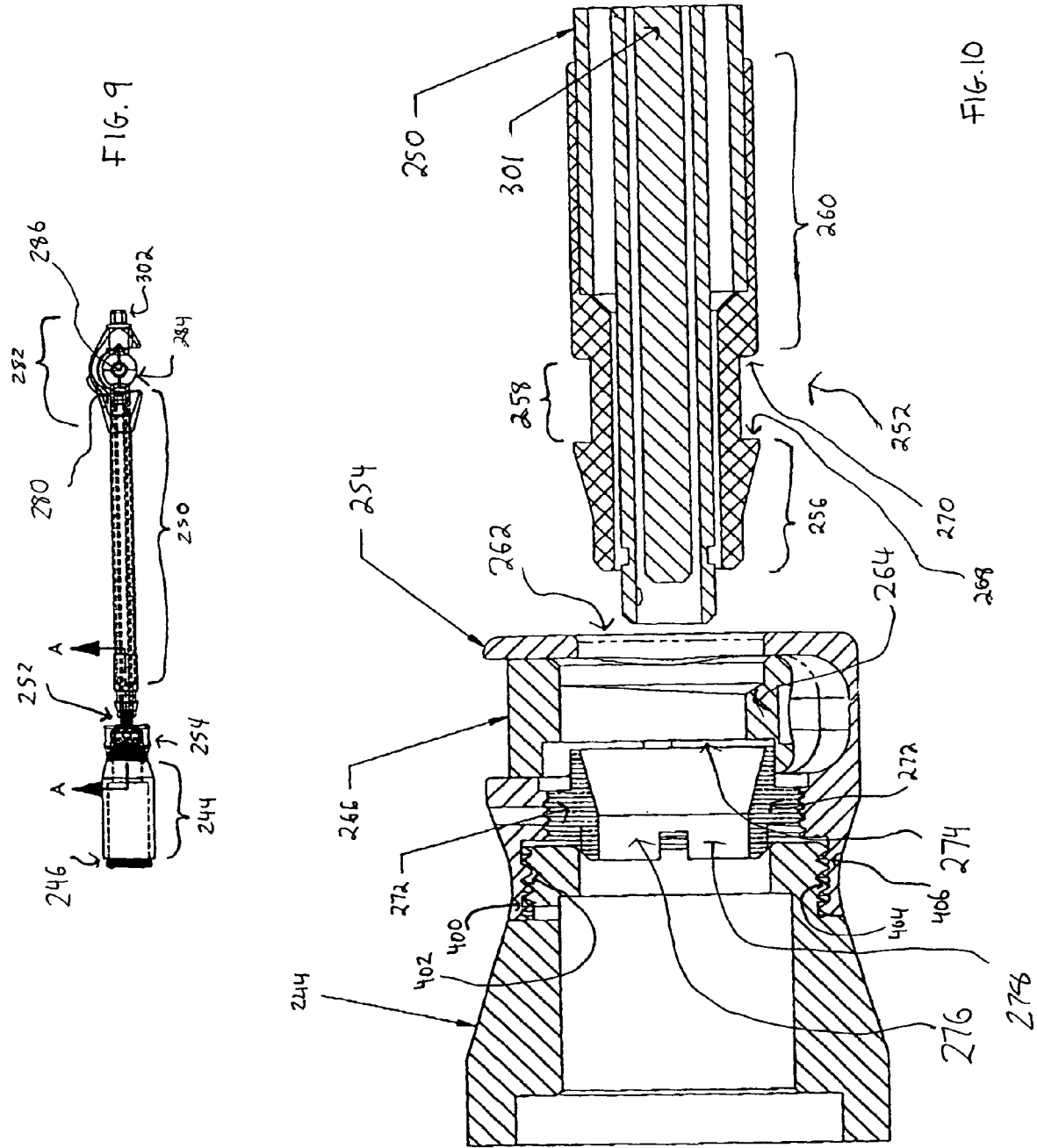

SURGICAL ARM ASSEMBLY INCLUDING QUICK CONNECT MECHANISM

This application is a continuation of U.S. application Ser. No. 10/040679, filed Nov. 8, 2001, abandoned.

BACKGROUND OF THE INVENTION

1. Field of the Invention

The present invention relates to medical devices, and, in particular, to a surgical arm system for positioning a medical instrument in connection with a surgical procedure. More particularly, the present invention provides such a surgical arm system, wherein the system includes at least one quick connect/release mechanism to expedite and facilitate disassembly and reassembly of the arm (e.g., for sterilization purposes), while ensuring that the arm functions reliably, has precise dimensions, and is structurally sound following each instance of disassembly and reassembly.

2. Description of Related Art

Most surgical procedures entail the active participation of several, and often many individuals, some of whom (e.g., one or more surgeons) have invaluable roles in the procedures, and still others who primarily represent a pair of free hands for assisting the surgeon(s).

Unfortunately, the physical presence of these assisting personnel necessarily causes crowding in the vicinity of the site (e.g., operating table) of the procedure. That, in turn, tends to create an environment of increased chaos during already stressful surgical procedures, and, arguably, leads to as many problems as are prevented by the presence of such individuals.

Recently, however, surgical arms have been developed that can substitute for these assisting personnel during certain medical procedures. In most instances, one or more of such arms are used (in lieu of such assisting personnel) to position and then hold in place one or more medical instruments at a fixed locus near or within a patient during a surgical procedure.

Such arms occupy much less space than medical personnel and, therefore, uncrowd the area at or near which a surgical procedure is occurring. This, however, is not their only benefit. Unlike medical personnel, these arms do not tire or flinch, are incapable of being distracted (e.g., by visual or aural stimuli, and/or by the need to eat, drink, or to use bathroom facilities), are not required to be trained or paid, and can be maneuvered and positioned with highly reliable accuracy, wherein their locus generally can be fixed and maintained for as long as desired by their operators.

Despite the benefits of such arms, they do suffer from one especially notable drawback; namely, they tend to be difficult to disassemble and, in particular to reassemble, e.g., to allow for sterilization thereof. This drawback affects many known surgical arms, such as the device depicted and described in U.S. Pat. No. 5,918,884 to Ognier ("the Ognier arm").

As shown in FIG. 1 (reproduced herein as FIG. 1) of U.S. Pat. No. 5,918,884, the Ognier arm includes several interconnected parts/segments that, when assembled, form a rather long arm with many curves and junctions that render the arm difficult/cumbersome to sterilize. Moreover, many of the components of the arm are hollow (i.e., have a lumen defined therein) and, therefore, require periodic cleaning.

In order to allow for simplified sterilization and/or cleaning thereof, such arms are generally at least partially disassembled/dismantled into smaller parts. This is problematic, however, because subsequent reassembly of such arms has proven to be a difficult and time-consuming process.

As shown in FIG. 5 of the Ognier patent (reproduced herein as FIG. 2), many of the parts of this arm are interconnected via threaded elements (e.g., nut ring 46) that must be threaded onto other elements (e.g., element 109) to reassemble the arm.

The thread patterns of these elements, however, hamper such reassembly. For example, the end of the element 109 to which the nut ring 46 attaches has a very fine, double pitched thread. This renders engagement of the nut ring 46 difficult, cumbersome, time consuming and, perhaps more significantly, may hinder the ability to distinguish (either audibly or visually) whether the nut ring is completely/properly engaged to the element.

And if any part of the Ognier surgical arm (or others like it) is improperly reassembled, there is a relatively high likelihood that the arm will not function optimally, or even acceptably.

For example, if a threaded element of the Ognier arm is not completely threaded into place, the arm may not be able to properly support the weight of the instrument(s) that it is designed/calibrated to hold. That, in turn, could compromise the ability of the arm to reliably hold the instrument(s) at all, let alone at a fixed locus.

The consequences of improper or suboptimal functioning of the Ognier arm are generally quite significant. If, for example, the arm malfunctions during a surgical procedure, the instrument may become detached from the arm. If that occurs, the instrument would fall from the arm and likely enter into the sterile field, where, during its descent, it could possibly contact and injure the patient and/or medical personnel.

And if the detached instrument does not contact the patient of any medical personnel, it will likely fall into the non-sterile field, thus necessitating sterilization prior to reuse. The delay that occurs during sterilization would likely necessitate potentially dangerous modification to the surgical procedure, and, in particular, the need for recalculation of the anesthesia dosage supplied to the patient.

Moreover, the detached instrument could become damaged during its fall from the arm such that, even if sterilized, it could not be further used in connection with the procedure. If this occurs and a replacement instrument is not nearby, the entire surgical procedure may be forced to be halted and postponed, thus resulting in potentially severe financial repercussions and, in some cases, moderate to serious adverse consequences to the short- or long-term prognosis of the patient.

Also, the mere possibility that such problems may occur can negatively affect a surgical procedure. If a surgeon is forced to worry about potential suboptimal functioning of the arm during a procedure, such a distraction could inhibit his/her confidence and ability to concentrate (and, in turn, his/her surgical performance) during the procedure.

Further, while some parts of the Ognier arm, when incorrectly or improperly reassembled, can cause serious problems to occur, still other parts of the arm are realistically incapable of disassembly by medical personnel given their training and the tools to which they have access.

For example, the compressed air inlet conduit 28 shown in FIGS. 2 and 3 (reproduced herein as, respectively, FIGS. 3 and 4) of the Ognier patent extends into, and is integral with the structure of a support block 106 to such an extent that it would require complete, non-trivial disassembly of the support block to allow for the compressed air inlet conduit to be detached therefrom.

Because of this, the conduit 28 tends not to be sterilized as frequently as it likely should. And even if sterilization of the conduit 28 does, in fact, occur, it is generally very difficult/cumbersome to successfully accomplish, and can, in some cases, compromise the structural integrity (i.e., cause kinking) of the conduit, which serves the important role of introducing pressurized gas into the arm to allow the arm to maintain a fixed locus.

Perhaps realizing the difficulty associated with sterilization of surgical arms such as the Ognier arm, some have determined that these types of surgical arms generally do not require frequent sterilization and/or cleaning because sleeves or other protective drapes are recommended. Despite the fact these arms do not directly contact any contaminants during a procedure, it is possible for the surgical arm to become contaminated by secondary exposure. This may occur through inadvertent exposure as a result of splashing or contact with contaminated gloves or drapes. As a result of this, it is necessary to sterilize surgical arms periodically. This requires the disassembly and reassembly of the surgical arms in order to use the surgical arm for extended periods of time and for multiple procedures.

Therefore, a need exists for a surgical arm that may be simply and expeditiously disassembled and reassembled by any member of a surgical team without difficulty and without requiring additional tools, while ensuring that the arm, following each subsequent disassembly and reassembly thereof, is structurally sound, properly dimensioned and able to function in a reliable manner.

SUMMARY OF THE INVENTION

The present invention provides a surgical arm that meets this, and other needs by including features that expedite and facilitate both disassembly and, in particular, reassembly of the arm while ensuring that the arm, upon each subsequent reassembly thereof, is structurally sound, properly dimensioned, and able to function in a reliable manner.

Disassembly and reassembly of the arm is greatly facilitated, as compared to conventional arms (such as that which is described and depicted in U.S. Pat. No. 5,918,844 to Ognier), by allowing for several components of the arm to be attached and disconnected via quick connect mechanisms.

A first of such mechanisms is effective to connect a gas supply conduit to a fitting that extends from a proximal housing of the arm. The mechanism advantageously allows for one-handed detachment of the conduit from the fitting, thus facilitating sterilization of the conduit.

In conventional arms, a distal end of this conduit is generally integral with this proximal housing, thus preventing (or rendering very difficult) complete detachment of the conduit. As such, in order to sterilize (e.g., in an autoclave) the conduit, it must be bent into a tight bend radius. Over time, this causes kinking of the conduit and, ultimately, failure of the conduit.

A second of such mechanisms is effective to place a distal rod of the arm into communication with a distal housing in a manner that not only ensures a reliable connection, but also that proper dimensions exist with reference to the rod and the housing.

In conventional arms, such a connection is achieved by threading complimentarily threaded elements together, which has proven difficult and time consuming due to the thread patterns of such elements as well as the need to precisely align the threads in order to allow for connection thereof. Moreover, even if the elements can be threaded, it is likewise difficult to discern by sight, sound or feel when/whether the complete threading has occurred. These problems are overcome through use of the second quick connection mechanism.

Still other aspects, embodiments and advantages of the present invention are discussed in detail below.

BRIEF DESCRIPTION OF THE DRAWINGS

For a fuller understanding of the nature and desired objects of the present invention, reference is made to the following detailed description taken in conjunction with the accompanying figures wherein like reference characters denote corresponding parts throughout the several views, and wherein:

FIG. 9 illustrates a top view of a distal portion of the surgical arm system of FIG. 5;

FIG. 10 illustrates cross-sectional view of a quick connect mechanism for bringing into communication the rod of FIG. 5 and the distal housing of FIG. 5;

DETAILED DESCRIPTION OF THE INVENTION

The present invention provides a surgical arm system for holding and positioning one or more instruments during a surgical procedure. The surgical arm includes at least one quick connect mechanism that beneficially allows for simple, yet reliable disassembly and reassembly of the arm by any member of a surgical team without difficulty and without requiring additional tools, but while still ensuring that, following reassembly, the arm is structurally sound, properly dimensioned, and capable of functioning in a highly reliable manner.

Figure 5:
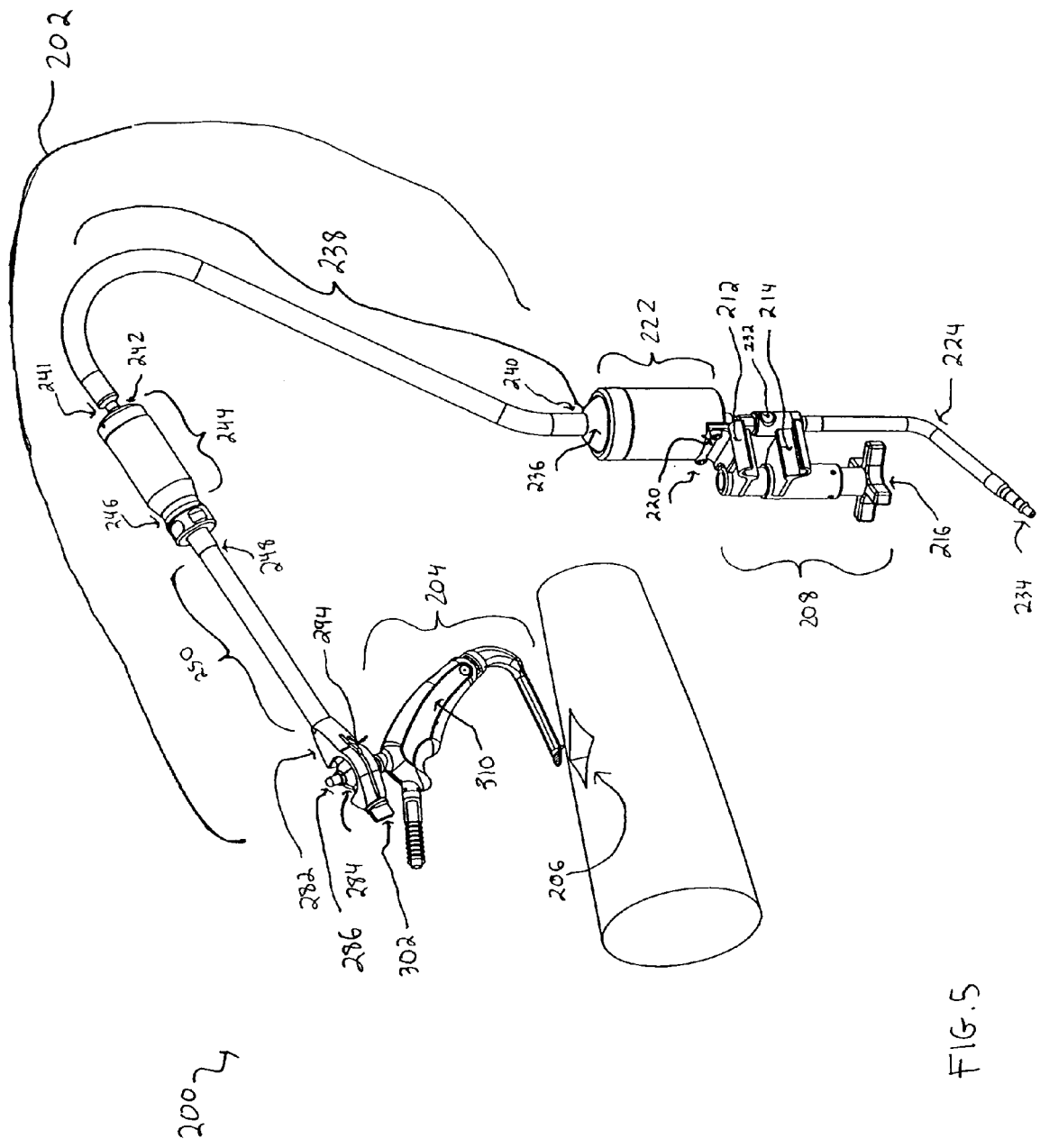
FIG. 5 illustrates a surgical setting in which a surgical arm system in accordance with the present invention may be utilized.

Referring initially to FIG. 5, a surgical system 200 in accordance with the present invention is shown and includes a surgical arm 202 that is effective to hold and selectively position a surgical instrument 204 and to selectively maintain the exact position of the instrument.

In the illustrated embodiment, the arm 202 is employed to position a retractor 204 within an incision site 206 in order to provide/facilitate access to the site by medical personnel (not shown) while performing, for example, a saphenous vein harvesting procedure during or prior to heart bypass surgery.

Although the system 200 of the present invention is depicted in FIG. 5 in connection with a saphenous vein harvesting procedure, it is understood that the system may be utilized in furtherance of a variety of different surgical procedures and, in particular, those in which it is necessary or advantageous to maneuver and reliably hold in place one or more medical/surgical instruments.

Also, in connection with the present invention, surgical instruments are understood to include not only conventional surgical devices, instruments and equipment of various sizes, shapes and utilities, but also any other equipment used in connection with a surgical or medical procedure, wherein such other equipment includes, but is not limited to, photographic, video, scoping and/or audio devices that record or transmit images, sound and/or other data from the surgical site and/or the vicinity, devices (including, but not limited to lasers) that provide light for illumination or treatment purposes, x-ray or ultrasonic devices, cauterizing equipment, and suturing devices.

As shown in FIG. 5 (and in more detail in FIG. 6), the system 200 includes a mounting area 208 for mounting the arm 202 to an object 210. This object 210 may be stationary or movable, wherein exemplary such objects include, but are not limited to, a table (e.g., an operating table) or a rail of a hospital gurney/bed.

Figure 6:
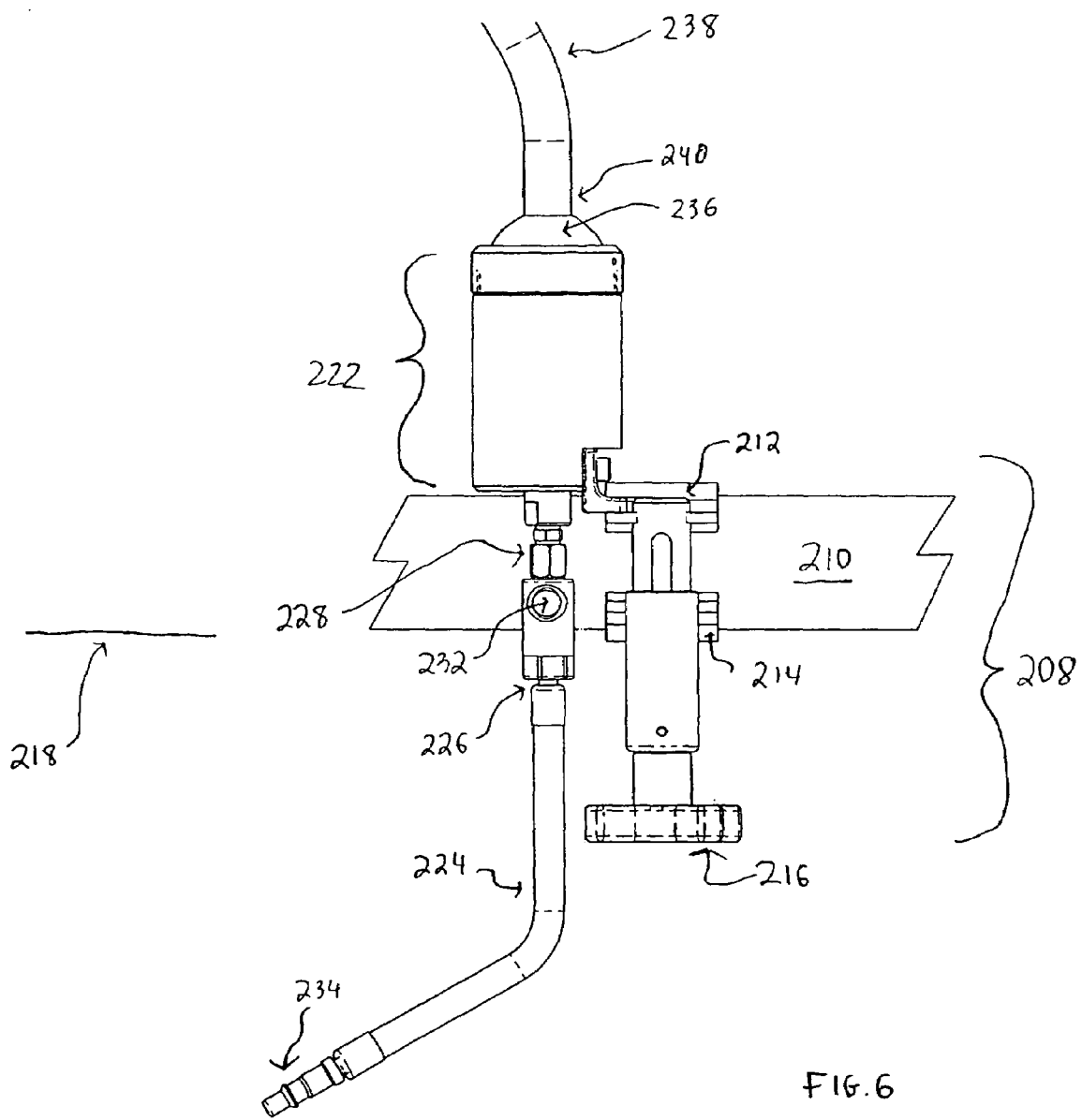
FIG. 6 illustrates an enlarged view of the mounting area of FIG. 5.

The mounting area 208 includes first and second mounting jaws/grippers 212, 214 that are reversibly movable to and from an open condition (as shown in FIG. 5) and a closed condition (as shown in FIG. 6), wherein the jaws are tightly, yet reversibly secured to the object 210 while in the latter condition.

The mounting jaws 212, 214 may be moved to and from their open and closed conditions (and to any intermediate positions) through the action (i.e., tightening and loosening) of a knob 216 or other appropriate actuating device or signal. Specifically, tightening (i.e., clockwise movement/turning) of the knob 216 is effective to move the jaws 212, 214 closer together, while loosening (i.e., counterclockwise movement/turning) of the knob is effective to move the jaws farther apart.

As shown in FIGS. 5 and 6, the knob 216 is positioned proximal to both of the mounting jaws 212, 214. Although alternate placement positions for the knob 216 are possible without departing from the scope of the invention, the placement position shown in FIGS. 5 and 6 is preferred because it allows the knob to be located in an area outside of the sterile field of the surgical setting, wherein this non-sterile area is defined as the space below (i.e., proximal to) line 218 in FIG. 6, and wherein the sterile field is defined as the space above (i.e., distal to) line 218 in FIG. 6. It is understood, however, that the position of line 218 may vary depending on the particulars of a surgical procedure.

In an embodiment wherein the knob 216 is located outside of the sterile field (i.e., in the non-sterile area), the knob may be beneficially operated by a non-sterile member of the surgical team without disturbing/compromising the sterile field during the procedure being performed, and such that other sterile members of the surgical team may remain unoccupied and/or free to concentrate on other tasks relating to the procedure.

Mounting area 208 is connected (e.g., via screws 220) to a first, proximal housing 222, with which a conduit 224 is in communication. The conduit 224 also is in communication with a gas source (not shown), which supplies pressurized gas (e.g., an inert gas, preferably $CO_2$, most preferably medical grade or United States Pharmacopia grade $CO_2$) to the system 200 to maintain the arm 202 in a substantially fixed position while holding the instrument 204.

The conduit may be made of a variety of materials, of which silicone (preferably reinforced with a polymer such as polyester) is an example.

Figure 1:
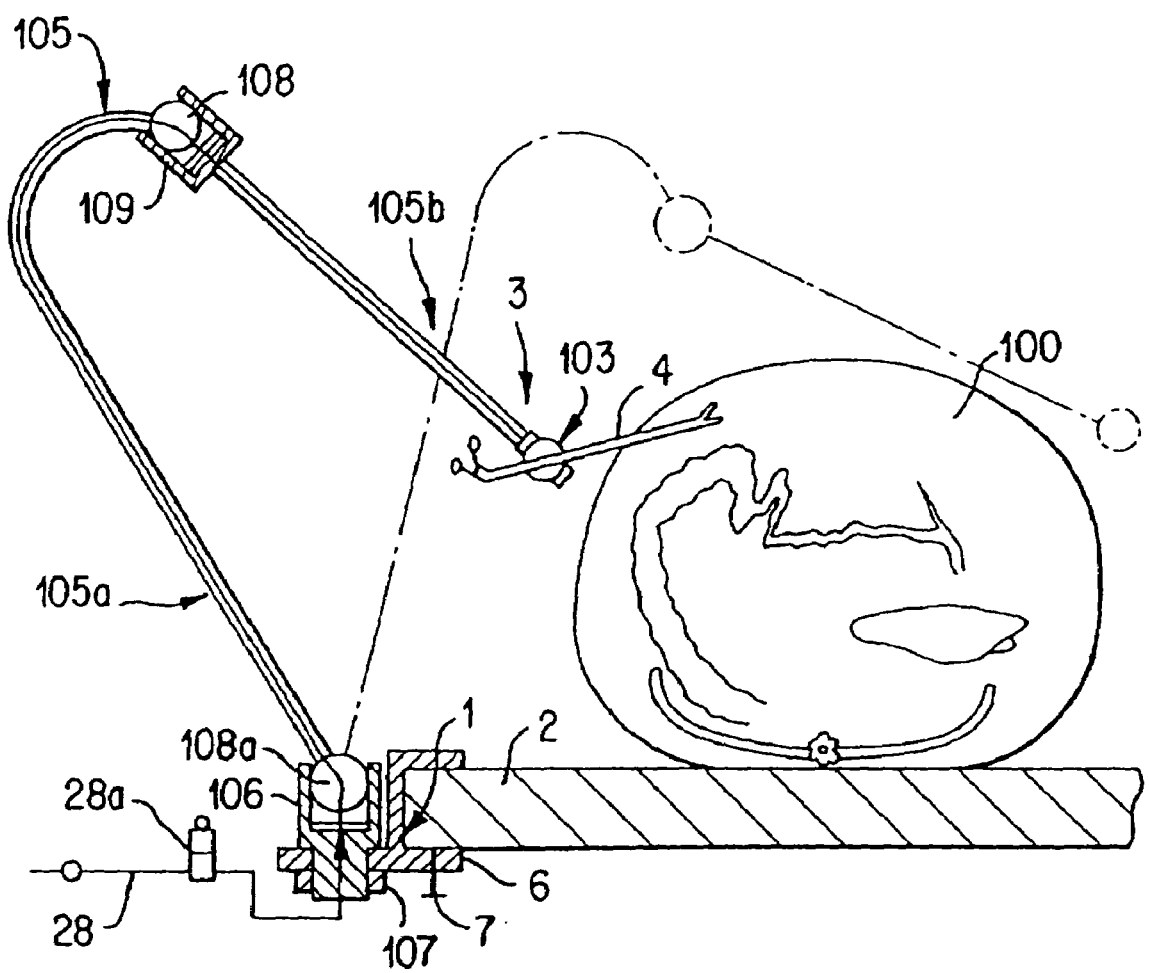
FIG. 1 illustrates a prior art surgical arm system in the context of a surgical setting.
Figure 2:
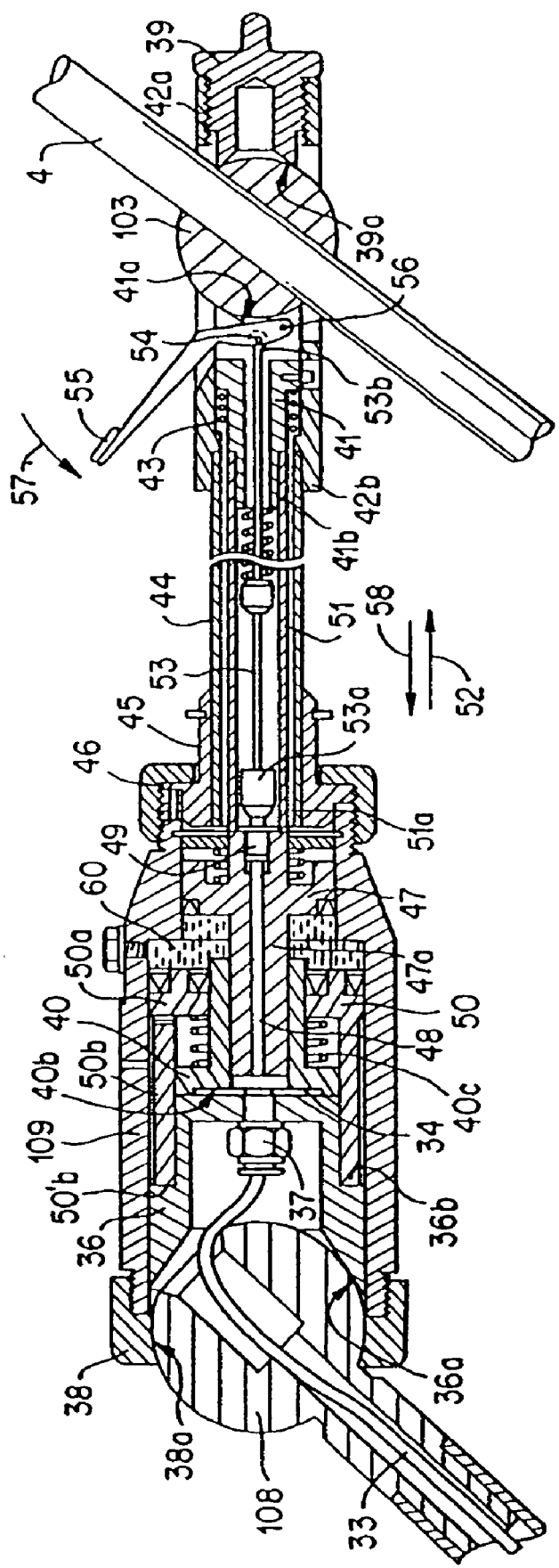
FIG. 2 illustrates a cross sectional view of the distal end of the arm of FIG. 1.
Figure 3:
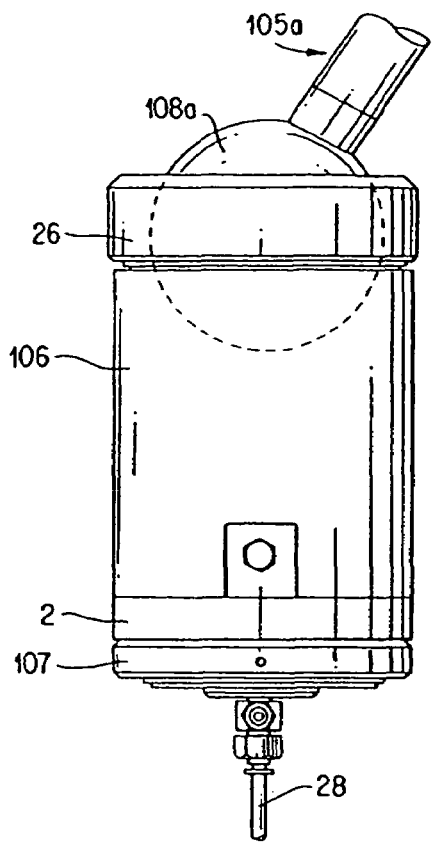
FIG. 3 illustrates a side elevational view of the proximal end of the arm of FIG. 1.
Figure 4:
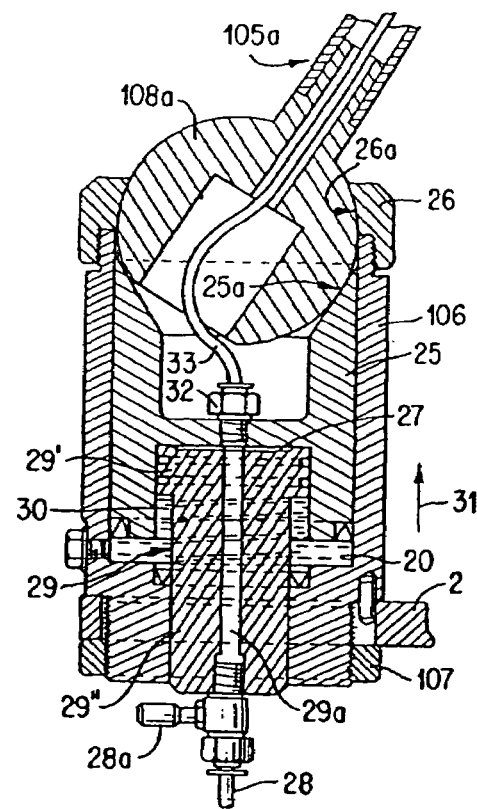
FIG. 4 illustrates a cross sectional view of the proximal end of the arm of FIG. 3.

To supply gas into and through the housing 222, a distal end 226 of the conduit 224 is placed into communication with a fitting 228 that extends into the housing. In conventional surgical arms, e.g., that which is depicted and described in U.S. Pat. No. 5,918,884 to Ognier (the disclosure of which is incorporated by reference in its entirety herein), the distal end of a gas conduit connects to, but also is integral with a housing (see FIGS. 2 and 3, which are reproduced herein, respectively, as FIGS. 3 and 4), thus rendering detachment of the conduit from the housing unduly difficult and time-consuming.

Figure 7:
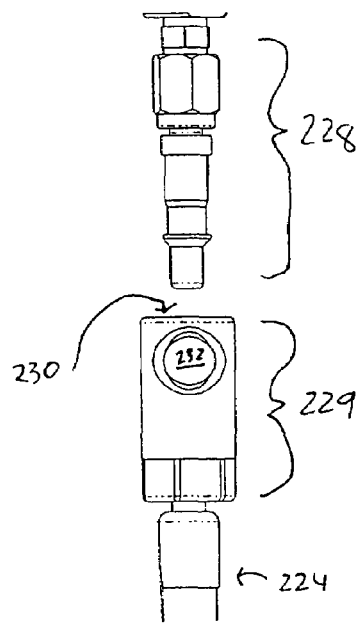
FIG. 7 illustrates a quick connect device for connecting a gas supply conduit to the system of FIG. 5.
Figure 8:
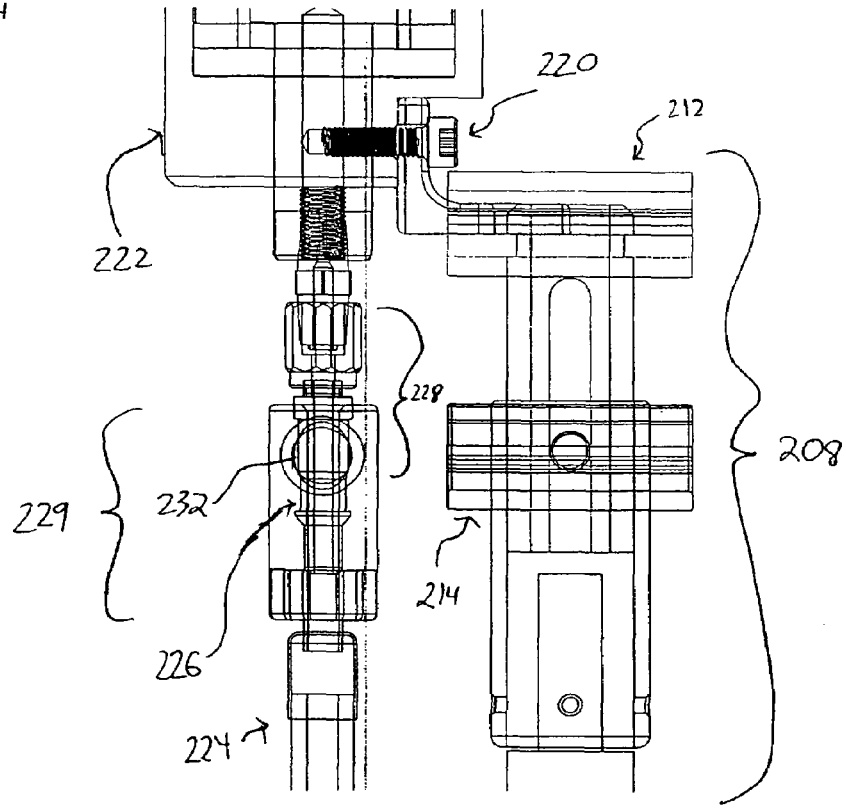
FIG. 8 illustrates a cross-sectional view of the quick connect device of FIG. 7 following connection of the conduit to the system via the device.

Although this type of integral connection may be utilized in this system 200, in accordance with an exemplary embodiment of the present invention (and as shown in FIGS. 7 and 8), the distal end 226 of the conduit 224 instead preferably connects to the fitting 228 via a quick connect device 229, which allows for one-handed attachment and removal of the conduit from the fitting.

To affect attachment, the fitting 228 is introduced into an opening 230 defined within the quick connect device 229, to which the distal end 226 of the conduit is also attached. Generally, attachment (e.g., via crimping) of the distal end 226 of the conduit 224 to the quick connect device 229 occurs prior to the device reaching an end user.

During its introduction into the quick connect device 229, the fitting 228 will engage a detent mechanism (not shown) within the quick connect device, thus causing an audible and/or tactile signal indicating that attachment has occurred and reversibly locking the fitting therewithin. FIG. 8 depicts the positional relationship between the conduit 224, the quick connect device 229, and the fitting 228 following such attachment.

To affect removal of the fitting 228 from the quick connect device 229, an operator depresses an actuator 232 (e.g., a button) located on the conduit. This (plus the force of gravity) may be enough to cause disengagement of the detent mechanism and, thus, the fitting 228. If not, the operator may be required to slightly pull upon the conduit (and/or the quick connect device 229) in a proximal direction while or after depressing the button to affect disengagement of the fitting 228. Even if necessary, however, this combined pressing and pulling action can advantageously be performed with one hand.

The proximal end 234 of the conduit 224 attaches to a gas source (not shown). This connection can be accomplished as is generally known in the art, but preferably is accomplished via a quick connect device similar to device 229.

Because the proximal end 234 of the conduit 224 and the distal end 226 of the conduit are able to be brought into, and removed from communication with, respectively, the fitting 228 and the pressurized gas source via quick connect devices, the entire conduit (with quick connect devices attached thereto) can be freely detached/removed from both of its attachment locations. Once completely detached (i.e., isolated) as such, the entire conduit 224 can be easily sterilized using standard options (e.g., autoclave).

If, as is shown in U.S. Pat. No. 5,918,884 to Ognier, the distal end of the conduit was integral with the housing into which it is inserted, the conduit could not be as readily isolated for sterilization. Instead, one would likely be forced to sterilize the conduit while it remained integral with the housing. This would likely necessitate bending and maneuvering of the conduit, which, over time (i.e., following repeated sterilizations of the conduit) will cause kinking of the conduit. Such kinking could, in turn, cause failure of the conduit, thus preventing (or at least significantly compromising) the ability of the conduit to deliver gas to the arm and, in turn, the ability of the arm to reliably hold an instrument in place during a surgical procedure.

Once the conduit 224 is brought into communication with the fitting 228, pressurized gas is able to travel from the gas source (not shown) through the conduit and into the first, proximal housing 222 (with which the fitting is also in communication). The gas flows through the housing 222 and into and through a ball 236 via a second conduit (not shown) as is generally known in the art, e.g., as is shown in FIG. 6.

This second conduit feeds the gas into a tube segment 238, a proximal end 240 of which is connected to the ball 236 seated within the first housing 222, and a distal end 238 of which is connected to a proximal end 242 of a second housing 244. These connections establish an airtight passage between the housings 222, 244 through which gas from the gas source can flow.

The shape of the tube segment 238 should be selected to provide for sufficient clearance between the first and second housings 222, 244. Also, the tube segment 238 should have an at least partially curved shape. A currently preferred shape for the tube segment 238 is the so-called "goose neck" orientation shown in FIG. 5, but other curved shapes/orientations may be selected as well without departing from the scope of the present invention.

Also, the tube segment 238 should be made of a strong, rigid material such that it can support the weight of both the instrument 204 held by the arm 202, and the portion of the arm located distal to the tube segment. By way of non-limiting example, the tube segment 238 can be made of steel (e.g., stainless steel, preferably 303 grade stainless steel).

The gas travels through the tube segment 238, and is introduced into a proximal end 242 of the second, distal housing 244 through a distal end 241 of the segment. The internal contents of the housing 244, as well as the role the housing plays with respect to the functioning of the arm 202 are generally similar to those of element 109 of the Ognier arm, which is depicted in FIG. 5 (reproduced herein as FIG. 2) of U.S. Pat. No. 5,918,884 to Ognier.

A distal end 246 of the second, distal housing 244 is in communication with a proximal end 248 of a rod portion 250 of the arm 202. In conventional arms, such communication is generally established by threading one or more elements onto one or more complimentarily threaded elements. For example, reference to FIG. 5 (reproduced herein as FIG. 2) of U.S. Pat. No. 5,918,884 to Ognier indicates that such a connection may be established by threading a nut ring 46 onto a complimentarily threaded portion an element 109.

This threading process is difficult, time consuming, and replete with inexactness. In the case of the arm disclosed in U.S. Pat. No. 5,918,884 to Ognier, the nut ring 46 has a very fine, double pitch thread that renders the threading process extremely difficult.

Moreover, even if one is able to thread the nut ring 46 to the element 109, it is difficult to distinguish (either visually, tactilely or audibly) whether the threading process has been performed such that the nut ring has been completely/properly threaded onto this element 109. And if the nut ring 46 is not completely threaded onto element 109, the ability of the arm to function properly can be compromised as discussed above.

In an exemplary embodiment of the present invention, the distal end 246 of the second, distal housing 244 and the proximal end 248 of the rod 250 are brought into communication through the use of a quick-connect mechanism as shown in FIGS. 9–12.

To effectuate this quick connection, a male quick connect member 252 is attached (e.g., via laser welding) to the rod 250 and a quick connect adapter 254 is attached to the distal housing 244. These attachments generally occur prior to delivery of the arm 202 to an end user—that is, medical personnel generally will not be required to assemble/attach either the member 252 to the rod 250 or the adapter 254 to the distal housing 244.

Figure 11:
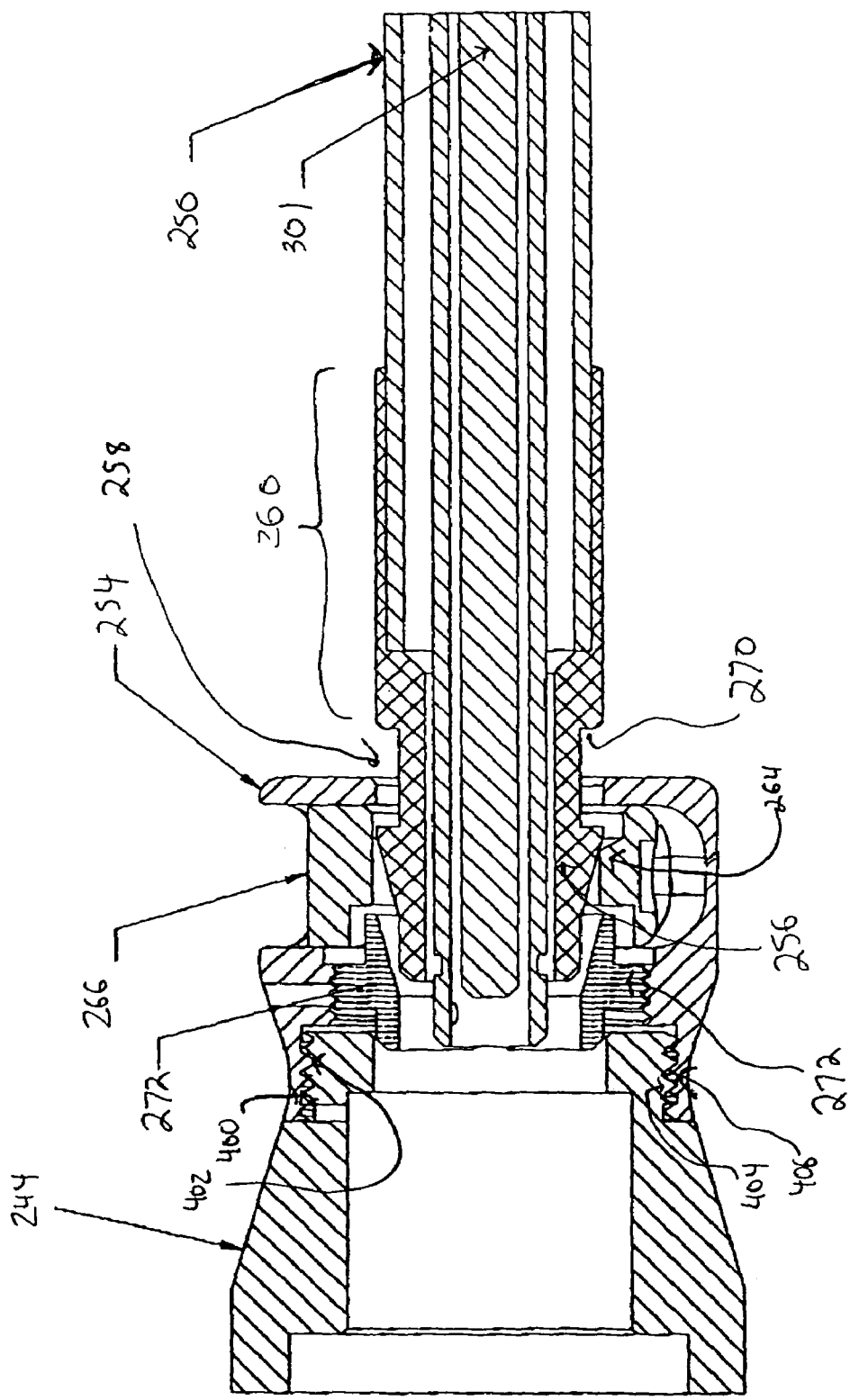
FIG. 11 illustrates a cross-sectional view of the quick connect mechanism of FIG. 10 during the connection process.
Figure 12:
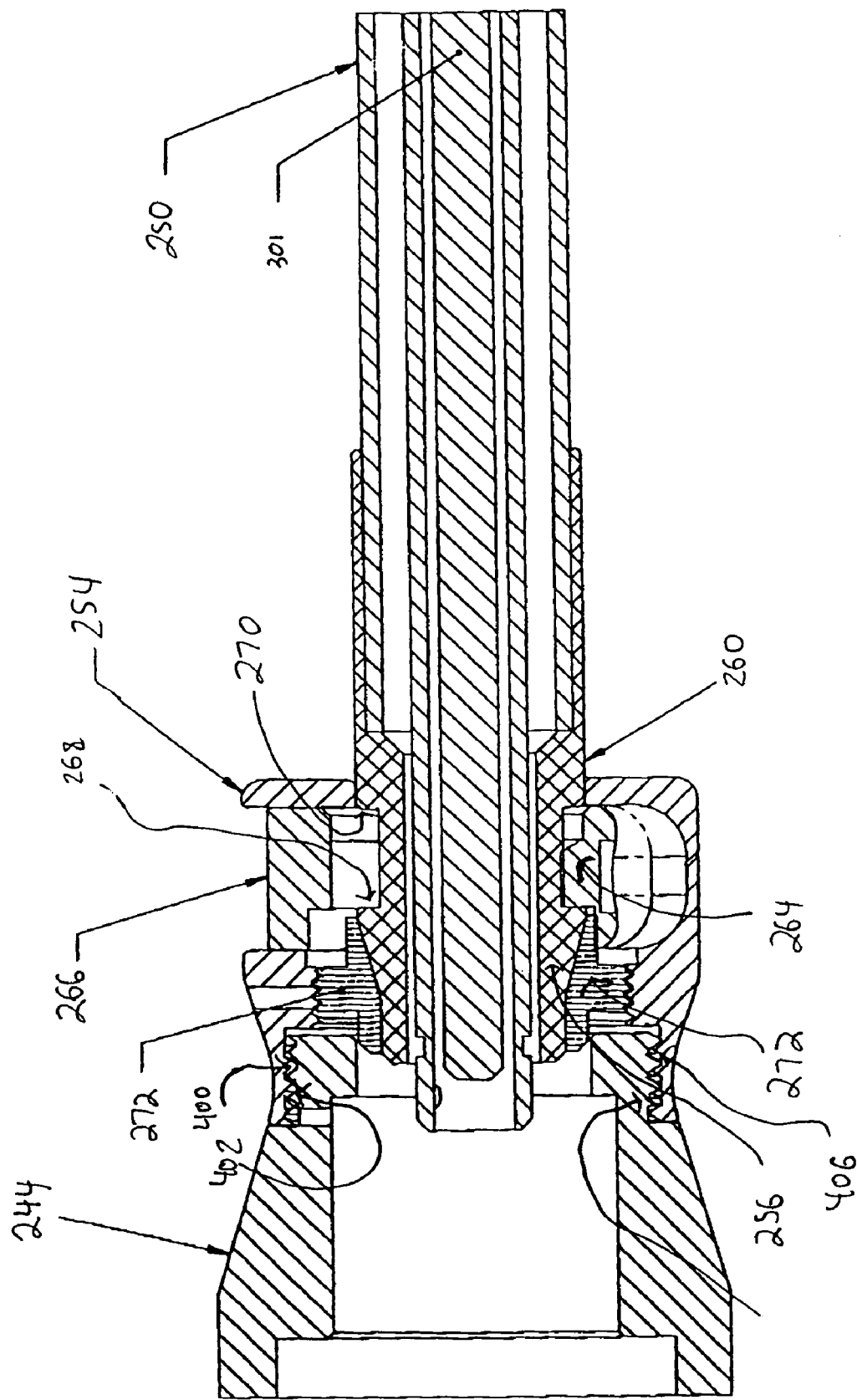
FIG. 12 illustrates a cross-sectional view of the quick disconnect mechanism of FIGS. 10 and 11 following the connection process.

As shown in FIGS. 10–12, attachment of the quick connect adapter 252 to the distal housing 244 is accomplished by threading the former onto the latter via complimentary threads 400, 402 and 404, 406. Although the adapter 252 is shown in these figures as being substantially completely threaded onto the housing 244, it is currently preferred that the threading be performed so as to define a gap (not shown) between the adapter and the housing.

The length of this gap, in turn, directly influences the amount of holding force the arm can withstand—that is, by lengthening and shortening the gap, one can modify how heavy of an instrument the arm can safely support.

The gap is generally established by the manufacturer by trial and error, wherein the size of the gap is modified by threading the adapter 252 closer too or farther from the housing 244 until the length of the gap is deemed appropriate for a particular instrument that the arm will ultimately be used to hold and support.

Thereafter, the threaded areas 400, 402 and 404, 406 are preferably treated with a sealant (preferably a liquid-based sealant or adhesive, wherein suitable sealants/adhesives are readily commercially available from companies such as Loctite of Rocky Hill, Conn., U.S.A.) to ensure that the length of the gap will not be accidentally modified by an end user.

The presence of this gap simulates the presence of a shim, which is generally present within the distal housing of arms such as that which is described and depicted in U.S. Pat. No. 5,918,844 to Ognier. In such arms, different shims of various thicknesses are placed (one at a time) within the housing to modify the holding force of the arm. Insertion and removal of each shim, however, requires very time consuming disassembly and subsequent reassembly of the housing within which it is placed.

Such shim-related problems are avoided in accordance with the present invention by being able to simulate the gap-creating function of the shim without actually requiring the presence of a shim, or, for that matter, any other physical object. Instead, the gap is created and modified by threading the adapter 252 closer to and/or farther from the distal housing 244.

At no time during establishment or modification of the gap is the distal housing 244 required to be even partially (let alone completely) disassembled. This greatly simplifies and expedites the process of readying the arm 202 for shipment to an end user.

Referring now to the male quick connect member 252, it generally includes three differently shaped regions—a bell-shaped distal region 256, a recessed intermediate region 258, and a proximal region 260. The number and/or the shape or one, some or all of these regions 256, 258, 260 may vary, however, without departing from the scope of the present invention.

During introduction of the member 252 (see FIG. 11) into a proximal opening 262 defined within the adapter 254, the bell-shaped region 256 contacts a ramp area 264 of the adapter. The ramp 264 is in communication with a spring (not shown), which is compressed in response to the force exerted by the male quick connect member 252 during its distal advancement into the adapter 254.

As the spring is compressed, both the ramp 264 and an actuator (e.g., a button) 266 to which the spring is coupled are depressed as shown by the changes in position of each of these elements from FIG. 10 to FIG. 11.

As shown in FIG. 12, once the bell-shaped region 256 of the male quick connect member 252 has been advanced distally beyond the ramp 264, the force being exerted by the member upon the ramp (and, therefore, upon the spring) is discontinued/removed, thus causing the spring to recoil and, in turn, causing not only the ramp to be inserted/placed within the intermediate region 258 of the member, but also causing the button to return to its FIG. 10 position.

Because of the shape of the ramp 264 and of the walls 268, 270 of the recessed, intermediate region 258 of the member 252, the ramp, once it is located within the intermediate region is, in essence, locked therein. This locked state, however, is reversible upon the combined action of depressing the button 266 and proximally pulling upon the male quick connect member 252 to free the ramp 264 from within the intermediate region 258 of the member, thus enabling detachment the member from the quick connect adapter 254.

Connection and detachment of the quick connect member 252 to the quick connect adapter 254 can advantageously be accomplished through the use of a simple push and locate feature. This is in stark contrast to arms (such as that which is described and depicted in U.S. Pat. No. 5,918,844 to Ognier) that involve/entail complex threaded connections and that, therefore, require significant effort, concentration and time to detach and, in particular, to subsequently reattach.

Moreover, such threaded connections must also be precisely aligned in order to affect connection thereof. Such precise alignment is not necessary in order to attach the member 252 and adapter 254.

Rather, all that must be done to ensure precise alignment is to introduce the male quick connect member 252 into the opening 262 defined within the quick connect adapter 254 and then distally guide the member into the adapter. Even if the member 252 and the adapter 254 are not precisely aligned as the former is being introduced into the latter, the internal shape of the adapter and the shape of the bell region 256 of the male quick connect member 252 will force proper alignment of the member upon continued distal advancement of the member into the adapter.

As shown in FIG. 12, the housing 244 also includes a stop disk 272, the physical presence of which is effective to limit the distal advancement of the bell-shaped region 256 of the male quick connect member 252. The presence of the stop disk 272 (which generally, and preferably, is placed within the housing 244 prior to the arm 202 reaching an end user) also defines a dimensional gap 274 (see FIG. 10) within the housing.

Prior to the arm 202 reaching an end user, the dimensions of this gap 274 will have been established and/or adjusted (i.e., lengthened or shortened) by maneuvering one or more adjustment slots 276, 278 (e.g., via a screw driver). By properly dimensioning the gap 274, one can eliminate most, if not all axial play (i.e., so called "slop") with respect to the button 266, wherein such axial play, if present, could interfere with an end user's ability to manipulate the button.

Because the position of the stop disk 272 and the dimensions of the gap 274 are established prior to delivery of the arm 202 to an end user, attachment of the quick connect member 252 to the quick connect adapter 252 is not only simple to perform, but also is always assured to result in an exact, desirable positional relationship between the rod 250 (which is in communication with the male quick connect member 252) and the housing 244 (which is in communication with the quick connect adapter 254).

Conventional arms (such as the arm disclosed and depicted in U.S. Pat. No. 5,918,844 to Ognier) instead rely upon threading to establish similar connections. As such, it is difficult to discern, either by sight, sound and/or touch, when (or even whether) these connections have been established, let alone with exact dimensions.

Conversely, once the bell-shaped region 256 of the male quick connect member 252 passes distally beyond the ramp 264, the ramp will audibly return (due to the recoiling of the spring) into its uncompressed state, thus preventing the member from moving in a proximal direction. And the quick connect member 252 is prevented from moving in a distal direction by the presence of the stop disk 272. Collectively, this ensures that once the quick connect member 252 is reversibly locked within the quick connect adapter 254, a proper positional/dimensional relationship automatically exists between the member (and, therefore, the rod 250 attached thereto) and the adapter (and, thus, the housing 244 attached thereto).

The stop disk 272, button 266, male quick connect member 252 and quick connect adapter 254 may be made of a variety of materials. In an exemplary embodiment of the present invention, each of these elements 252, 254, 266, 272 is made of steel, preferably stainless steel, most preferably 303 grade stainless steel.

Referring once again to FIG. 5, the distal end 280 of the rod 250 is attached to a shaped holding element 282, which holds a ball 284 in which an instrument 204 is retained as will be explained in further detail below. Generally, both the rod 250 and the holding element 282 should be made of strong, rigid materials such that they can support the weight of the instrument 204. By way of non-limiting example, either or both the rod 250 and the retaining element 282 can be made of steel (e.g., stainless steel, preferably 303 grade stainless steel).

The holding element 282 may have a variety of shapes, but should be shaped to allow for the ball 284 to be freely inserted and removed therefrom in at least one direction. In an exemplary embodiment of the present invention, the holding element 282 is a C-shaped clamp, thus allowing for insertion and removal of the ball 284 in any of three different directions (i.e., upwardly, downwardly, and through the C-shaped opening).

Figure 13:
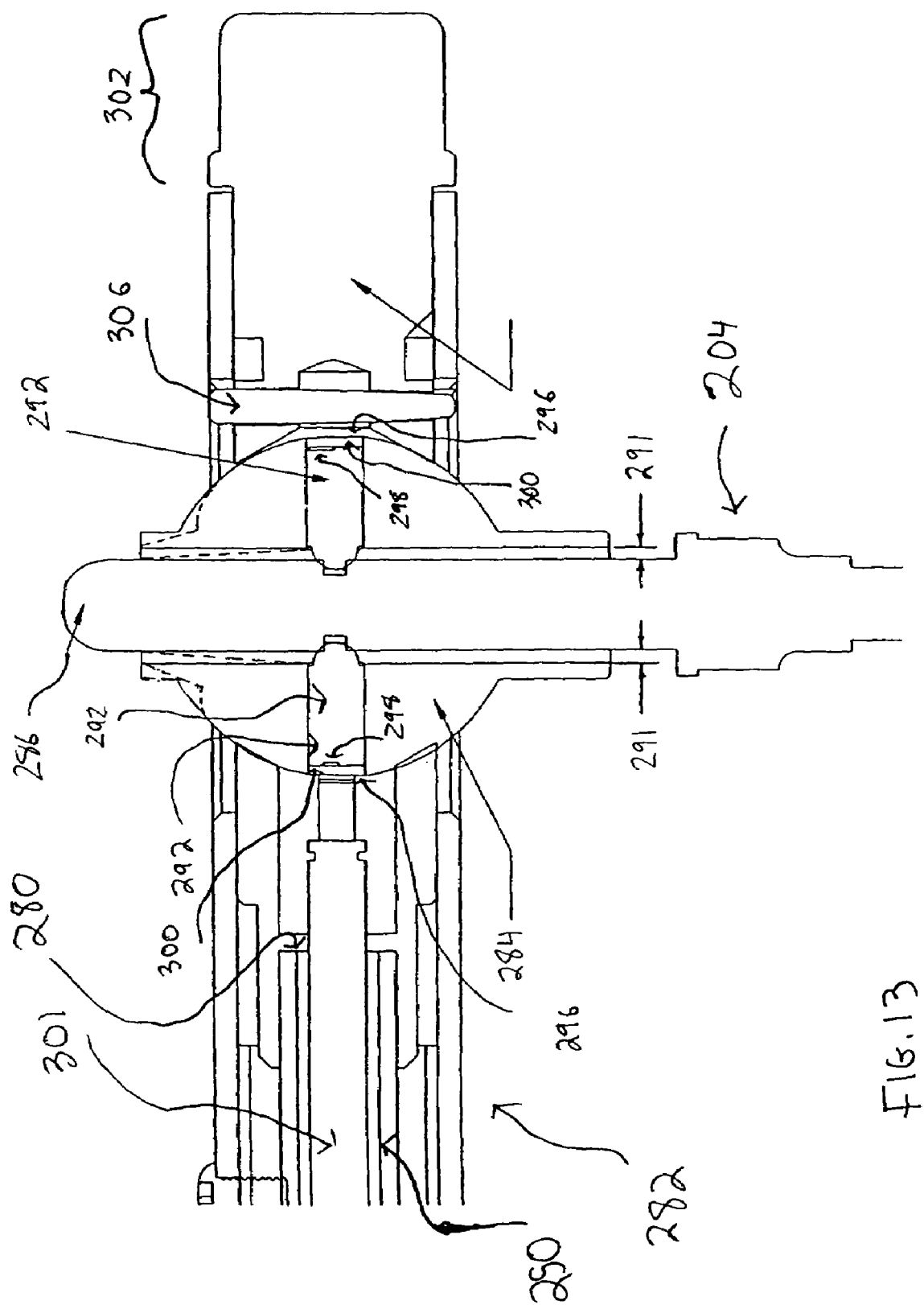
FIG. 13 is an enlarged, side view of the holding element of FIG. 5 with the ball held therewithin and with an instrument being retained within the ball.

The holding element 282 is shown in FIG. 13 with the ball 284 having been inserted therein and with the proximal end 286 of the instrument 204 having been inserted within the ball. In this exemplary embodiment, the instrument 204 is a retractor and its proximal end 286 is a retractor post.

The ball 284 (shown in detail in FIG. 14) is retained within the holding element 282 due to the internal components of the ball, the presence of a ball retaining element/ guard 288, and by virtue of a supply of pressurized gas that flows from the gas source, through the arm 202, and into the ball.

Figure 14:
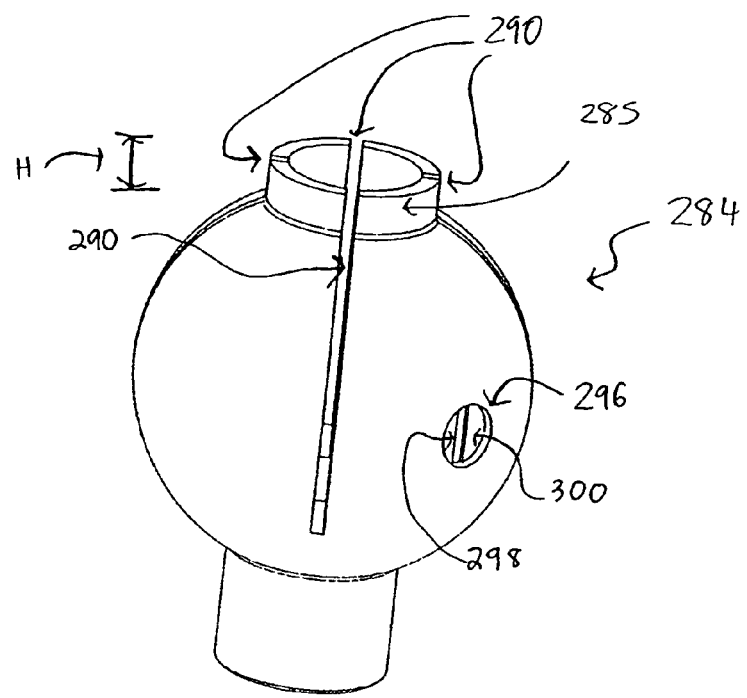
FIG. 14 is an enlarged view of the ball of FIG. 13.
Figure 15:
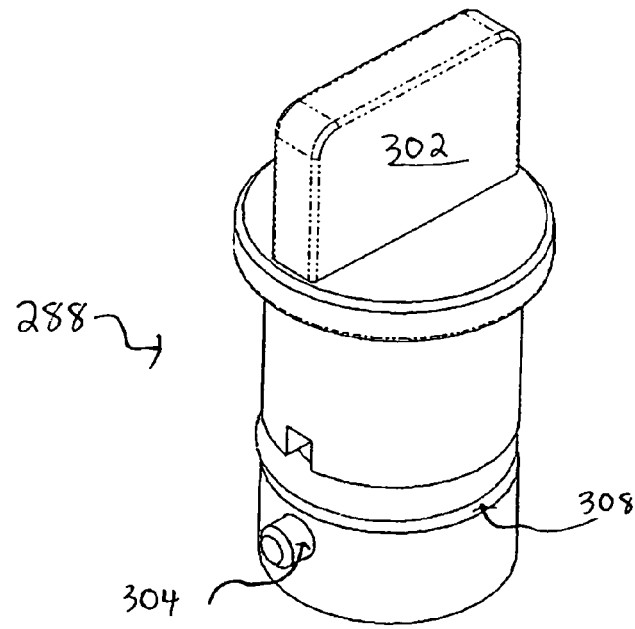
FIG. 15 is an enlarged view of the retaining element of FIG. 13.

As best shown in FIG. 14, the ball includes a post 285 with a height, H. The height, H, of the post 285 is generally in the range of about 0.1 to 0.2 inch, preferably in the range of about 0.1 to 0.15 inch, most preferably about 0.12 inch. Thus, this height, H, is about 0.25 inch less than that of comparable balls included in arms such as that which is disclosed in U.S. Pat. No. 5,918,844 to Ognier.

By virtue of its post 285 having a small height, H, the ball (while in a relaxed state) can freely rotate within the holding element 282 without fear of the post contacting (i.e., being impeded by) the holding element. This ensures that the instrument 204 (while contained within the ball) can enjoy a similarly large freedom of movement and that, in turn, the instrument is able to assume a wider range of positions and orientations with respect to the incision site 206 as compared to conventional arms.

The other dimensions of the ball 284 may vary so long as they allow for it to fit within the holding element 282 and for the instrument 204 to fit within the ball. Generally, the ball has an overall length in the range of about 1.0 inch to 2.0 inches (preferably about 1.5 inch), and a diameter while in a relaxed state in the range of about 1.0 to 1.5 inch, preferably about 1.2 inch.

As indicated in FIG. 14, there is at least one slit 290 defined within the ball while it is in a relaxed state. The presence of each of these slits 290 defines a clearance gap 291 between the ball and the proximal end 286 of the instrument. Although four such slits are depicted in FIG. 14, the number of slits present may be greater or less than four without departing from the scope of the present invention. In an embodiment wherein four slits 290 are present, they are preferably spaced apart from each other by approximately 90°.

The delivery of pressurized gas into the ball 284 (which may be accomplished as is generally known in the art, e.g., as discussed in U.S. Pat. No. 5,918,844 to Ognier) causes the ball to shift from a relaxed, non-pressurized state (shown in FIGS. 13 and 14) to a pressurized state (shown by the dotted lines in FIG. 13).

Once the ball 284 is pressurized by the gas from the gas source, the ball is caused to shrink (see dotted lines in FIG. 13), thus closing the slits 290 and removing the clearance gaps 291. The shrinking of the ball 284 also causes one or more spring-loaded retention guards 292 to be firmly pressed against the instrument 204, thus ensuring that the instrument will be reliably retained within the ball 284 and that the position of the instrument with respect to the ball will not change while the gas is being supplied to the ball.

Generally, the number of guards 292 included within the ball 284 is two, but may instead be zero, one or greater than two. Preferably, there is an even number of guards 292 included within the ball 284.

The guards 292 may be introduced into the ball 284 as is generally known in the art. By way of non-limiting example, each guard 292 may be inserted within (or removed from) an opening 296 defined within the ball and threaded into (or out of) place through the action of a screwdriver (not shown) upon one or more slots 298 defined on outer ends 300 of the guard.

The supply of gas to the ball 284 can be freely initiated, interrupted or resumed through the action of an actuator 294 (e.g., a lever) as depicted in FIG. 5. If the lever is actuated, the drain tube 301 within the rod 250 (see FIG. 9) is distally advanced so as to trigger a valve (not shown), such as a Schraeder valve, that allows the gas to escape as is generally known in the art, thus removing the pressure from the ball 284 and causing the ball to return to its relaxed state.

Even in this relaxed state, however, the instrument 204 can reliably be retained within the ball 284. This is because the spring-loaded retention guards 292 are positioned within the ball 284 such that when the ball is in a relaxed state, the guards are in contact with the proximal end 288 (e.g., the post) of the instrument 204 wherein they exert enough force upon the instrument to define a transitional fit between the guards and the instrument. This fit is strong enough to support the weight of the instrument 204, and, therefore, to prevent the instrument from falling out of the ball 284, but also not so strong that the instrument cannot be easily removed from the ball via the application of a moderate pulling force by an operator if that is so desired.

In order to provide still further assurance that the instrument 204 will not fall out of the ball 284 while the ball is in a relaxed (i.e., non-pressurized) state, a retaining element 288 may be placed into communication with the ball. As shown in FIG. 5, the retaining element 288 is inserted within the holding element 282 such that a gripping portion 302 of the retaining element protrudes from the holding element.

As shown in FIG. 13, a pin 306 is at least partially housed within the retaining element 288. In this exemplary embodiment, the pin 306 spans the diameter of the retaining element 288 and protrudes therefrom at two protrusions 304, each of which is located approximately 180° apart from the other on the outer periphery of the retaining element.

By inserting the retaining element 288 within the holding element 282 and then using the gripping portion 302 to rotate the retaining element approximately 90° in either a counterclockwise or clockwise direction, these protrusions 304 are caused to be inserted within seats (not shown) defined within the holding element 282. Once this occurs, the pin 306 assumes a position (as shown in FIG. 13) against the ball, thus further deterring the ball (and, therefore, the instrument 204 retained therewithin) from falling out of the holding element 282.

In an exemplary embodiment of the present invention, the retaining element 288 also includes an O-ring 308 around its circumference, the presence of which creates a transitional fit between the retaining element and the holding element 282 when the protrusions 304 are not within the seats in the holding element. This transitional fit is effective to prevent unwanted/inadvertent detachment of the retaining element 288 from the holding element 282, but also allows for removal of the retaining element if desired through the application of a moderate pulling force by an operator upon the gripping portion 302.

Absent this O-ring 308, the retaining element 288, when its protrusion(s) 304 are not contained within the seat(s) within the holding element 282, could somewhat easily become dislodged and, in turn, fall into the surgical field, thus disturbing the surgeon and/or the incision site 206 during the procedure. The O-ring may be made of a variety of materials having varying characteristics. Exemplary such materials include, but are not limited to, a plastic material (e.g., a thermoplastic rubber such as Viton®, which is commercially available from Dupont Dow Elastomers of Wilmington, Del., U.S.A.).

The retaining element 288 should have dimensions that allow it to fit within the holding element 282 as described above. Generally, the retaining element 288 has a length in the range of about 1.0 inch to 2.0 inches, preferably about 1.5 inch, wherein the length of the gripping element 302 generally comprises less than half the overall length of the retaining element. Preferably, the length of the gripping element 302 is in the range of about 0.5 to 0.7 inch.

The diameter of the retaining element 288 is generally in the range of about 0.5 inch to about 1.0 inch, preferably about 0.70 inch and is generally greatest at the O-ring 308 and the protrusions 304.

The surgical arm system 200 described above and depicted in FIGS. 5–15 may be used in connection with numerous surgical procedures in order to maneuver a surgical instrument 204 and to reliably maintain the position of the surgical arm 202 near/within a surgical site 206.

Prior to utilizing the system 200, its components are disassembled for sterilization as described above, then sterilized as is generally known in the art (e.g., via autoclaving), and reassembled also as discussed above. It is understood, however, that these steps need not be performed if circumstances dictate that sterilization is not required.

The ball 284, if not already in position within the holding element 282, is inserted therewithin, after which the instrument 204 is placed within the ball 284. The retaining element 288 can then be inserted within the holding element 282 as described above either following the insertion of the instrument 204 or prior thereto.

Thereafter, the arm 202 is maneuvered to its desired position by gripping the arm at its tube segment 238 and/or its rod 250 and then moving the arm to its desired position. Optionally, such maneuvering can instead be accomplished by gripping and moving the instrument 204 itself. In the illustrated embodiment of FIG. 5, for example, the instrument 204 includes an area 310 (e.g., a handle) that may be grasped by an operator to position the arm 202 with which the instrument is in communication.

If the instrument 204 is used to position the arm 202 as such, the retaining element 288 preferably should be in place and should have previously been rotated 90° as described above to lessen the likelihood that the instrument will fall out of the ball 284 during the positioning process. Otherwise, the retaining element should be so rotated prior to pressurization of the arm 202.

Once the instrument 204 is in a desired position, the gas source is activated and the lever 294 is released to allow for gas to enter (and, therefore, pressurize) the ball 284. This, as noted above, causes the instrument 204 to be securely held in place within the ball 284, thus ensuring that the instrument will retain a fixed locus and will not fall out of the ball.

If it is desired to change the position of the instrument 204, the lever 294 should be moved (i.e., actuated) to allow gas to escape from the system, thus allowing for movement of the instrument and the other components of the arm 202. Discontinuing the supply of pressurized gas to the arm 202 will also allow one to remove the instrument 204 if so desired, e.g., to replace the instrument with another instrument or a different size and/or type.

The foregoing description of the invention is merely illustrative thereof, and it is understood that variations and modifications can be effected without departing from the scope or spirit of the invention as set forth in the following claims. All documents mentioned herein are incorporated by reference herein in their entirety.

What is claimed is:

1. A surgical arm system, comprising:
a mounting component for mounting the surgical arm system to an object;
a holding component holding a retaining element that is sized and shaped to retain a portion of a predetermined surgical instrument therein and wherein the retaining element includes an opening defined therein, wherein the opening is sized to accommodate a proximal end of the surgical instrument and at least one retention guard disposed within the retaining element, wherein each of the at least one retention guard is in contact with the surgical instrument while the retaining element is in a first position so as to define a transitional fit between each of the at least one guard and the surgical instrument and wherein the retaining element is transitionable to and from the first position by, respectively, supplying and discontinuing a supply of a pressurized gas to the retaining element;
a plurality of arm segments for connecting the mounting component to the holding component, the plurality of arm segments including first and second components, the first component being connectable to the second component;
a quick connect member attached to one of the first component or second component; and
a quick connect adapter attached to the other one of the first component or the second component and having a stop disk, a ramp and actuator attached thereto, wherein the quick connect member is shaped to be insertable within the quick connect adapter to bring the first component or the second component into communication with the other of the first component or the second component,
wherein such insertion is effective to cause the ramp and the actuator to be at least partially depressed from a first of each of the ramp and actuator positions to a depressed second position, and such that continued insertion of the quick connect member beyond a predetermined locus is effective to cause the ramp and actuator to return to their respective first positions to physically block separation of the quick connect member from the quick connect adaptor, and wherein the stop disk is positioned to substantially prevent movement of the quick connect member beyond the predetermined locus.

2. The surgical arm system of claim 1, wherein actuation of the actuator is effective to place the actuator and the ramp in their respective second positions to allow for removal of the quick connect member from the quick connect adapter via the application of a predetermined force upon at least a portion of the quick connect member.

3. The surgical arm system of claim 1, wherein lateral movement of the actuator is effective to place the actuator and the ramp in their respective second positions to allow for the removal of the quick connect member from the quick connect adaptor.

4. The surgical arm system of claim 1, wherein the mounting component is a mounting element that includes first and second mounting jaws between which the object is retained.

5. The surgical arm system of claim 4, further comprising: a knob in communication with the jaws, wherein movement of the knob in a first direction is effective to move the mounting jaws closer together and wherein movement of the knob in a second direction is effective to move the jaws further apart.

6. The surgical arm system of claim 1, wherein the surgical instrument is a retractor that is reasonably held by the holding component.

7. The surgical arm system of claim 1, wherein the quick connect member includes an enlarged region that, following insertion of the quick connect member beyond the predetermined locus, is located generally adjacent to the ramp on the quick connect adaptor.

8. The surgical arm system of claim 7, wherein the enlarged region on the quick connect member is substantially bell-shaped.

9. The surgical arm system of claim 7, wherein the quick connect member includes a recessed region generally adjacent to the enlarged region.

10. The surgical arm system of claim 9, wherein the ramp on the quick connect adaptor is positioned within the recessed region of the quick connect member upon returning to its first position following insertion of the quick connect member beyond the predetermined locus.

11. The surgical arm system of claim 1, wherein the holding component further comprises: a retaining element insertable within the holding element, the retaining element including a plurality of protrusions, wherein a pin extends between two of the plurality of protrusions, wherein a predetermined degree of rotation of the retaining element is effective to insert the protrusions into seats defined within the holding element such that the pin is placed into contact with the retaining element.

12. The surgical arm system of claim 11, wherein the predetermined degree of rotation is about 90°.

13. A surgical arm system, comprising:
  a mounting component at a first end of the surgical arm system;
    a holding component at a second end of the surgical arm system for holding a surgical instrument therein;
    a plurality of arm segments for connecting the mounting component to the holding component wherein a first arm segment includes a quick connect member thereon and a second arm segment includes a quick connect adaptor thereon, the first and second arm segments being reversibly attachable and detachable from each other via interoperation of the quick connect member and the quick connect adapter, and wherein the first and second arm segments are configured to allow a gas to pass therethrough when the quick connect adaptor and quick connect member are interconnected;
    the holding component including a ball-shaped member having a substantially spherically shaped outer surface and having an opening defined therein, wherein the opening is sized to accommodate a portion of the surgical instrument therein, the ball-shaped member having a diameter that is compressible to define engaging contact between the ball-shaped member and the surgical instrument and wherein the diameter of the ball-shaped member is movable between first and second positions by supplying and discontinuing a supply of pressurized gas through the first and second arm segments into the ball-shaped member.

14. The surgical arm system of claim 13, wherein the holding component further comprises: a retention guard insertable within the holding element, wherein the retention guard is movable in response to supplying or discontinuing the supply of a pressurized gas to the holding element.

15. The surgical arm system of claim 13, wherein the holding component further comprises: a retention guard insertable within the holding element, wherein the retention guard is biased to contact the surgical instrument in a first position of the retention guard.

16. The surgical arm system of claim 13, wherein the holding component further comprises: a retention guard insertable within the holding element, wherein the retention guard is biased to engage the surgical instrument in a second position of the retention guard.

17. The surgical arm system of claim 13, wherein the holding component has a predetermined degree of rotation of up to about 90°.

18. A surgical arm system, comprising:
  a quick connect system for bringing into communication a first component of the surgical arm system with a second component of the surgical arm system, the quick connect system comprising:
    a quick connect member attached to the first component; and
    a quick connect adapter attached to the second component and having an actuator attached thereto, wherein the quick connect member is shaped to be insertable into the quick connect adapter to bring the first component into communication with the second component and to allow a gas to flow therethrough, the first and second components being attachable and detachable from each other via interoperation of the quick connect member and the quick connect adapter; and
  a holding component on one of the first or second components of the surgical arm system holding a retaining element that is sized and shaped to retain a portion of a predetermined surgical instrument therein and wherein the retaining element includes an opening defined therein, wherein the opening is sized to accommodate a portion of the surgical instrument therein, and at least one retention guard disposed within the retaining element, wherein each of the at least one retention guard is in contact with the surgical instrument while the retaining element is in a first position so as to define a transitional fit between each of the at least one retention guard and the surgical instrument and wherein the retaining element comprises a ball shaped member having a substantially spherically shaped outer surface wherein the diameter of the ball shaped member is movable between first and second positions by supplying and discontinuing a supply of pressurized gas into the ball shaped member.

19. The surgical arm system of claim 18, wherein actuation of the actuator is effective to place the actuator in a first position to allow for removal of the quick connect member from the quick connect adapter via the application of a predetermined force upon the actuator of the quick connect member.

20. The surgical arm system of claim 19, wherein release of the actuator is effective to allow the actuator to return to a second position wherein the quick connect member and the quick connect adapter are interconnected to allow for the supply of a pressurized gas to the retaining element.

21. The surgical arm system of claim 18, wherein the holding component further comprises: a retention guard insertable within the holding element, wherein the retention guard is biased to contact the surgical instrument in a first position of the retention guard.

22. The surgical arm system of claim 18, wherein the holding component further comprises: a retention guard insertable within the holding element, wherein the retention guard is biased to engage the surgical instrument in a second position of the retention guard.

23. A surgical arm system, comprising:
  a quick connect system for bringing into communication a first component of the surgical arm system with a second component of the surgical arm system the quick connect system comprising:

a quick connect member attached to the first component and including a substantially ball-shaped member and an adjacent recessed region;

a quick connect adapter attached to the second component and having an actuator attached thereto, wherein the quick connect member is shaped to be insertable into the quick connect adapter to bring the first component into communication with the second component to allow the supply of a gas therethrough;

wherein such insertion is effective to cause the movement of the actuator from a first position thereof, and such that continued insertion of the quick connect member beyond a predetermined locus is effective to cause the actuator to return to the first position and to physically block separation of the quick connect member from the quick connect adaptor;

a holding component on one of the first or second components of the surgical arm system holding a retaining element that is sized and shaped to retain a portion of a predetermined surgical instrument therein and wherein the retaining element includes an opening defined therein, wherein the opening is sized to accommodate a portion of the surgical instrument therein and at least one retention guard disposed within the retaining element, wherein the retaining element comprises a ball shaped member wherein the diameter of the ball shaped member is movable between first and second positions by supplying and discontinuing a supply of pressurized gas to the ball shaped member.

* * * * *

UNITED STATES PATENT AND TRADEMARK OFFICE
CERTIFICATE OF CORRECTION

| | | |
|---|---|---|
| PATENT NO. | : 7,021,854 B2 | |
| APPLICATION NO. | : 10/720143 | |
| DATED | : April 4, 2006 | |
| INVENTOR(S) | : Dana A. Oliver et al. | |

It is certified that error appears in the above-identified patent and that said Letters Patent is hereby corrected as shown below:

<u>Column 14</u>
Line 13, please delete "for";

<u>Column 16</u>
Line 66, please insert --,-- after "system".

Signed and Sealed this

First Day of August, 2006

JON W. DUDAS
*Director of the United States Patent and Trademark Office*